(12) United States Patent
Møller

(10) Patent No.: US 8,298,194 B2
(45) Date of Patent: Oct. 30, 2012

(54) INJECTION DEVICE AND A METHOD OF CHANGING A CARTRIDGE IN THE DEVICE

(75) Inventor: Claus Schmidt Møller, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 585 days.

(21) Appl. No.: 12/282,442

(22) PCT Filed: Feb. 23, 2007

(86) PCT No.: PCT/EP2007/051757
§ 371 (c)(1),
(2), (4) Date: Mar. 19, 2009

(87) PCT Pub. No.: WO2007/104636
PCT Pub. Date: Sep. 20, 2007

(65) Prior Publication Data
US 2009/0254027 A1    Oct. 8, 2009

Related U.S. Application Data
(60) Provisional application No. 60/784,779, filed on Mar. 22, 2006.

(30) Foreign Application Priority Data
Mar. 10, 2006 (EP) ...................................... 06004933

(51) Int. Cl.
*A61M 5/00* (2006.01)
*A61M 5/315* (2006.01)
*A61M 5/30* (2006.01)

(52) U.S. Cl. .......... 604/207; 604/224; 604/71; 604/234; 604/232; 604/181

(58) Field of Classification Search ............... 604/71–72, 604/207–211, 224, 68, 232–235, 181, 187
See application file for complete search history.

(56) References Cited

U.S. PATENT DOCUMENTS
854,399 A    5/1907   Bridge
(Continued)

FOREIGN PATENT DOCUMENTS
AU    2003232576    1/2004
(Continued)

OTHER PUBLICATIONS
Final Rejection mailed on Dec. 13, 2010 in U.S. Appl. No. 12/571,721, filed Oct. 1, 2009 by Glejbol et al.
(Continued)

*Primary Examiner* — Nicholas Lucchesi
*Assistant Examiner* — Rebecca E Eisenberg
(74) *Attorney, Agent, or Firm* — Wesley A. Nicolas

(57) ABSTRACT

A refillable injection device (1) having a dose setting mechanism with a dose setting member (4) and a dose rod (11). The dose setting member and the dose rod engage during normal operation of the injection device, and they do not engage during change of cartridge. The dose setting member and the dose rod need to be moved into engagement when a new cartridge is inserted in the injection device. Thereby there is a risk that stress is build-up in the piston rod. In order to prevent this, the cartridge holder is operatively connected to the dose rod in such a manner that when a cartridge is being inserted in the cartridge holder, the dose rod is caused to move along with the piston rod in an axial direction, at least while the dose setting member and the dose rod are moved into engagement.

13 Claims, 6 Drawing Sheets

U.S. PATENT DOCUMENTS

| | | | |
|---|---|---|---|
| 2,392,196 A | 1/1946 | Smith | |
| 2,956,563 A | 10/1960 | Sarnoff | |
| 3,110,310 A | 11/1963 | Cislak | |
| 3,115,135 A | 12/1963 | Sarnoff | |
| 3,144,178 A * | 8/1964 | Sarnoff | 222/327 |
| 3,556,099 A | 1/1971 | Knight et al. | |
| 3,880,162 A | 4/1975 | Simmons | |
| 3,944,843 A | 3/1976 | Vaz Martins | |
| 4,026,288 A | 5/1977 | Costa et al. | |
| 4,231,368 A | 11/1980 | Becker | |
| 4,275,727 A | 6/1981 | Keeri-Szanto | |
| 4,277,227 A | 7/1981 | Jenkins | |
| 4,298,000 A | 11/1981 | Thill et al. | |
| 4,300,554 A | 11/1981 | Hessberg et al. | |
| 4,313,439 A | 2/1982 | Babb et al. | |
| 4,314,556 A | 2/1982 | Ma | |
| 4,368,731 A | 1/1983 | Schramm | |
| RE31,315 E | 7/1983 | Jenkins et al. | |
| 4,393,723 A | 7/1983 | Brand | |
| 4,430,079 A | 2/1984 | Thill et al. | |
| 4,465,478 A | 8/1984 | Sabelman et al. | |
| 4,470,317 A | 9/1984 | Sabloewski et al. | |
| 4,493,704 A | 1/1985 | Beard et al. | |
| 4,498,904 A | 2/1985 | Turner et al. | |
| 4,515,584 A | 5/1985 | Abe et al. | |
| 4,568,335 A | 2/1986 | Updike et al. | |
| 4,585,439 A | 4/1986 | Michel | |
| 4,634,431 A | 1/1987 | Whitney et al. | |
| 4,676,122 A | 6/1987 | Szabo et al. | |
| 4,749,109 A | 6/1988 | Kamen | |
| 4,812,724 A | 3/1989 | Langer et al. | |
| 4,833,379 A | 5/1989 | Kaibel et al. | |
| 4,838,860 A | 6/1989 | Groshong et al. | |
| 4,865,591 A | 9/1989 | Sams | |
| 4,871,351 A | 10/1989 | Feingold | |
| 4,883,472 A | 11/1989 | Michel | |
| 4,893,291 A | 1/1990 | Bick et al. | |
| 4,898,578 A | 2/1990 | Rubalcaba | |
| 4,919,596 A | 4/1990 | Slate et al. | |
| 4,936,833 A | 6/1990 | Sams | |
| 4,950,246 A | 8/1990 | Muller | |
| 4,973,318 A | 11/1990 | Holm | |
| 4,988,337 A | 1/1991 | Ito | |
| 4,994,033 A | 2/1991 | Shockey et al. | |
| 5,000,744 A | 3/1991 | Hoffman et al. | |
| 5,002,537 A | 3/1991 | Hoffman et al. | |
| 5,064,098 A | 11/1991 | Hutter et al. | |
| 5,078,698 A | 1/1992 | Stiehl et al. | |
| 5,104,388 A | 4/1992 | Quackenbush | |
| 5,112,317 A | 5/1992 | Michel | |
| 5,113,869 A | 5/1992 | Nappholz et al. | |
| 5,114,406 A | 5/1992 | Gabriel et al. | |
| 5,135,485 A | 8/1992 | Cohen et al. | |
| 5,163,904 A | 11/1992 | Lampropoulos et al. | |
| 5,176,646 A | 1/1993 | Kuroda | |
| 5,207,752 A | 5/1993 | Sorenson et al. | |
| 5,221,268 A | 6/1993 | Barton et al. | |
| 5,226,342 A | 7/1993 | Panin | |
| 5,226,895 A | 7/1993 | Harris | |
| 5,226,896 A | 7/1993 | Harris | |
| 5,244,461 A | 9/1993 | Derlien | |
| 5,244,465 A | 9/1993 | Michel | |
| 5,246,417 A | 9/1993 | Haak et al. | |
| 5,257,987 A | 11/1993 | Athayde et al. | |
| 5,271,527 A | 12/1993 | Haber et al. | |
| 5,279,585 A | 1/1994 | Balkwill | |
| 5,279,586 A | 1/1994 | Balkwill | |
| 5,281,198 A | 1/1994 | Haber et al. | |
| 5,284,480 A | 2/1994 | Porter et al. | |
| 5,292,976 A | 3/1994 | Dessau et al. | |
| 5,295,976 A | 3/1994 | Harris | |
| 5,304,152 A | 4/1994 | Sams | |
| 5,308,340 A | 5/1994 | Harris | |
| 5,314,412 A | 5/1994 | Rex | |
| 5,318,540 A | 6/1994 | Athayde et al. | |
| 5,320,609 A | 6/1994 | Haber et al. | |
| 5,331,954 A | 7/1994 | Rex et al. | |
| 5,368,572 A | 11/1994 | Shirota | |
| 5,370,629 A | 12/1994 | Michel et al. | |
| 5,378,233 A | 1/1995 | Haber et al. | |
| 5,383,856 A | 1/1995 | Bersin | |
| 5,383,865 A | 1/1995 | Michel | |
| 5,440,976 A | 8/1995 | Giuliano et al. | |
| 5,445,606 A | 8/1995 | Haak et al. | |
| 5,447,150 A | 9/1995 | Bacon | |
| 5,478,316 A | 12/1995 | Bitdinger et al. | |
| 5,480,387 A | 1/1996 | Gabriel et al. | |
| 5,492,534 A | 2/1996 | Athayde et al. | |
| 5,496,286 A | 3/1996 | Stiehl et al. | |
| 5,505,697 A | 4/1996 | McKinnon, Jr. et al. | |
| 5,505,704 A | 4/1996 | Pawelka et al. | |
| 5,536,249 A | 7/1996 | Castellano et al. | |
| 5,546,932 A | 8/1996 | Galli | |
| 5,549,575 A | 8/1996 | Giambatista et al. | |
| 5,573,729 A | 11/1996 | Belgardt et al. | |
| 5,582,598 A | 12/1996 | Chanoch | |
| 5,584,815 A | 12/1996 | Pawelka et al. | |
| 5,591,136 A | 1/1997 | Gabriel | |
| 5,593,390 A | 1/1997 | Castellano et al. | |
| 5,599,314 A | 2/1997 | Neill | |
| 5,611,783 A | 3/1997 | Mikkelsen | |
| 5,611,784 A | 3/1997 | Barresi et al. | |
| 5,626,566 A | 5/1997 | Petersen et al. | |
| 5,628,309 A | 5/1997 | Brown | |
| 5,637,095 A | 6/1997 | Nason et al. | |
| 5,645,052 A | 7/1997 | Kersey | |
| 5,662,612 A | 9/1997 | Niehoff | |
| 5,674,204 A | 10/1997 | Chanoch | |
| 5,679,111 A | 10/1997 | Hertman et al. | |
| 5,681,285 A | 10/1997 | Ford et al. | |
| 5,685,864 A | 11/1997 | Shanley et al. | |
| 5,688,251 A | 11/1997 | Chanoch | |
| 5,709,662 A | 1/1998 | Olive et al. | |
| 5,716,990 A | 2/1998 | Bagshawe et al. | |
| 5,720,733 A | 2/1998 | Brown | |
| 5,725,508 A | 3/1998 | Chanoch | |
| 5,728,074 A | 3/1998 | Castellano et al. | |
| 5,728,559 A | 3/1998 | Nilsson et al. | |
| 5,741,211 A | 4/1998 | Renirie et al. | |
| 5,743,889 A | 4/1998 | Sams | |
| 5,755,692 A | 5/1998 | Manicom | |
| 5,782,633 A | 7/1998 | Mühlbauer | |
| 5,807,334 A | 9/1998 | Hodosh et al. | |
| 5,814,022 A | 9/1998 | Antanavich et al. | |
| 5,820,602 A | 10/1998 | Kovelman et al. | |
| 5,823,998 A | 10/1998 | Yamagata | |
| 5,827,232 A | 10/1998 | Chanoch | |
| 5,843,036 A | 12/1998 | Olive et al. | |
| 5,879,360 A | 3/1999 | Crankshaw | |
| 5,879,630 A | 3/1999 | Lescouzeres et al. | |
| 5,882,718 A | 3/1999 | Pommer et al. | |
| 5,898,028 A | 4/1999 | Jensen et al. | |
| 5,921,966 A | 7/1999 | Bendek et al. | |
| 5,928,201 A | 7/1999 | Poulsen et al. | |
| 5,933,671 A | 8/1999 | Stephany et al. | |
| 5,938,642 A | 8/1999 | Burroughs et al. | |
| 5,947,934 A | 9/1999 | Hansen et al. | |
| 5,951,530 A | 9/1999 | Steengaard et al. | |
| 5,954,689 A | 9/1999 | Poulsen | |
| 5,954,700 A | 9/1999 | Kovelman | |
| 5,957,889 A | 9/1999 | Poulsen et al. | |
| 5,961,496 A | 10/1999 | Nielsen et al. | |
| 5,971,963 A | 10/1999 | Choi | |
| 5,980,491 A | 11/1999 | Hansen | |
| 5,984,900 A | 11/1999 | Mikkelsen | |
| 5,989,221 A | 11/1999 | Hjertman | |
| 5,998,989 A | 12/1999 | Lohberg | |
| 6,003,736 A | 12/1999 | Ljunggren | |
| 6,004,297 A | 12/1999 | Steenfeldt-Jensen et al. | |
| 6,010,485 A | 1/2000 | Buch-Rasmussen et al. | |
| 6,033,376 A | 3/2000 | Rockley | |
| 6,033,377 A | 3/2000 | Rasmussen et al. | |
| 6,036,675 A | 3/2000 | Thorne et al. | |
| 6,048,336 A | 4/2000 | Gabriel | |
| 6,074,372 A | 6/2000 | Hansen et al. | |
| 6,083,197 A | 7/2000 | Umbaugh | |
| 6,086,567 A | 7/2000 | Kirchhofer et al. | |

| | | | | | | |
|---|---|---|---|---|---|---|
| 6,096,010 | A | 8/2000 | Walters | 2002/0052578 A1 | 5/2002 | Moller |
| 6,110,148 | A | 8/2000 | Brown et al. | 2002/0077852 A1 | 6/2002 | Ford et al. |
| 6,110,149 | A | 8/2000 | Klitgaard et al. | 2002/0107486 A1 | 8/2002 | Munk |
| 6,129,080 | A | 10/2000 | Pitcher et al. | 2002/0120235 A1 | 8/2002 | Enggaard |
| 6,146,361 | A | 11/2000 | DiBiasi et al. | 2002/0165500 A1 | 11/2002 | Bechtold et al. |
| 6,159,161 | A | 12/2000 | Hodosh | 2002/0173752 A1 | 11/2002 | Polzin |
| 6,161,364 | A | 12/2000 | Kolberg | 2002/0188250 A1 | 12/2002 | Landau et al. |
| 6,193,698 | B1 | 2/2001 | Kirchhofer et al. | 2003/0009133 A1 | 1/2003 | Ramey |
| 6,221,046 | B1 | 4/2001 | Burroughs et al. | 2003/0039679 A1 | 2/2003 | Duirs |
| 6,221,053 | B1 | 4/2001 | Walters et al. | 2003/0073954 A1 | 4/2003 | Moberg et al. |
| 6,231,540 | B1 | 5/2001 | Smedegaard | 2003/0114800 A1 | 6/2003 | Veasey et al. |
| 6,235,004 | B1 | 5/2001 | Steenfeldt-Jensen et al. | 2003/0172924 A1 | 9/2003 | Staniforth et al. |
| 6,245,046 | B1 | 6/2001 | Sibbitt | 2003/0176871 A1 | 9/2003 | Pavlov et al. |
| 6,248,090 | B1 | 6/2001 | Jensen et al. | 2003/0216663 A1 | 11/2003 | Willuhn et al. |
| 6,248,095 | B1 | 6/2001 | Giambatista et al. | 2003/0233075 A1 | 12/2003 | Huegli et al. |
| 6,258,062 | B1 | 7/2001 | Thielen et al. | 2004/0010204 A1 | 1/2004 | Weber et al. |
| 6,268,722 | B1 | 7/2001 | Kogure et al. | 2004/0024361 A1 | 2/2004 | Fago |
| 6,269,340 | B1 | 7/2001 | Ford et al. | 2004/0051368 A1 | 3/2004 | Caputo et al. |
| 6,277,097 | B1 | 8/2001 | Mikkelsen et al. | 2004/0059299 A1 | 3/2004 | Moller |
| 6,277,098 | B1 | 8/2001 | Klitmose et al. | 2004/0108339 A1 | 6/2004 | Hansen et al. |
| 6,281,225 | B1 | 8/2001 | Hearst et al. | 2004/0158304 A1 | 8/2004 | Cory et al. |
| 6,283,941 | B1 | 9/2001 | Schoenfeld et al. | 2004/0171983 A1 | 9/2004 | Sparks et al. |
| 6,287,283 | B1 | 9/2001 | Ljunggreen et al. | 2004/0186431 A1 | 9/2004 | Graf et al. |
| 6,302,869 | B1 | 10/2001 | Klitgaard | 2004/0207385 A1 | 10/2004 | Gafner et al. |
| 6,312,413 | B1 | 11/2001 | Jensen et al. | 2004/0210199 A1 | 10/2004 | Atterbury et al. |
| 6,340,357 | B1 | 1/2002 | Poulsen et al. | 2004/0230157 A1 | 11/2004 | Perry et al. |
| 6,364,860 | B1 | 4/2002 | Steck et al. | 2004/0236282 A1 | 11/2004 | Braithwaite |
| 6,379,339 | B1 | 4/2002 | Klitgaard et al. | 2004/0249348 A1 | 12/2004 | Wimpenny et al. |
| 6,383,167 | B2 | 5/2002 | Kirchhofer et al. | 2004/0260247 A1 | 12/2004 | Veasey et al. |
| 6,391,005 | B1 | 5/2002 | Lum et al. | 2004/0267207 A1 | 12/2004 | Veasey et al. |
| 6,419,661 | B1 | 7/2002 | Kuhr et al. | 2004/0267208 A1 | 12/2004 | Veasey et al. |
| 6,514,230 | B1 | 2/2003 | Munk et al. | 2005/0004529 A1 | 1/2005 | Veasey et al. |
| 6,537,251 | B2 | 3/2003 | Klitmose | 2005/0019400 A1 | 1/2005 | Deveney et al. |
| 6,547,755 | B1 | 4/2003 | Lippe et al. | 2005/0033244 A1 | 2/2005 | Veasey et al. |
| 6,547,763 | B2 | 4/2003 | Steenfeldt-Jensen et al. | 2005/0055011 A1 | 3/2005 | Enggaard |
| 6,547,764 | B2 | 4/2003 | Larsen et al. | 2005/0197625 A1 | 9/2005 | Haueter et al. |
| 6,562,011 | B1 | 5/2003 | Buch-Rasmussen et al. | 2005/0205083 A1 | 9/2005 | Staniforth et al. |
| 6,569,126 | B1 | 5/2003 | Poulsen et al. | 2005/0209570 A1 | 9/2005 | Møller |
| 6,582,404 | B2 | 6/2003 | Klitgaard et al. | 2005/0268915 A1 | 12/2005 | Wassenaar et al. |
| 6,585,698 | B1 | 7/2003 | Packman et al. | 2006/0118612 A1 | 6/2006 | Christoffersen et al. |
| 6,599,272 | B1 | 7/2003 | Hjertman et al. | 2006/0258988 A1 | 11/2006 | Keitel et al. |
| 6,605,067 | B1 | 8/2003 | Larsen | 2006/0264838 A1 | 11/2006 | Volckmann |
| 6,613,019 | B2 | 9/2003 | Munk | 2007/0093761 A1 | 4/2007 | Veasey |
| 6,663,602 | B2 | 12/2003 | Moller | 2007/0244445 A1 | 10/2007 | Moller |
| 6,666,849 | B1 | 12/2003 | Marshall et al. | 2008/0065026 A1 | 3/2008 | Moller |
| 6,673,033 | B1 | 1/2004 | Sciulli et al. | 2008/0221530 A1 | 9/2008 | Glejbol et al. |
| 6,692,472 | B2 | 2/2004 | Hansen et al. | 2008/0281275 A1 | 11/2008 | Moller |
| 6,699,224 | B2 | 3/2004 | Kirchhofer et al. | 2009/0043264 A1 | 2/2009 | Glejbol et al. |
| 6,716,198 | B2 | 4/2004 | Larsen | 2009/0062748 A1 | 3/2009 | Moller et al. |
| 6,726,661 | B2 | 4/2004 | Munk et al. | | | |
| 6,752,798 | B2 | 6/2004 | McWethy et al. | | FOREIGN PATENT DOCUMENTS | |
| 6,770,288 | B2 | 8/2004 | Duirs | CA | 2359375 | 7/2000 |
| 6,796,970 | B1 | 9/2004 | Klitmose et al. | DE | 3048135 | 7/1982 |
| 6,852,404 | B2 | 2/2005 | Kuwajima et al. | DE | 3236374 | 4/1984 |
| 6,887,238 | B2 | 5/2005 | Jahns et al. | DE | 36 09 555 | 9/1987 |
| 6,893,415 | B2 | 5/2005 | Madsen et al. | DE | 3638984 | 5/1988 |
| 6,899,698 | B2 | 5/2005 | Sams | DE | 3923079 | 1/1991 |
| 6,899,699 | B2 | 5/2005 | Enggaard | DE | 4223958 | 1/1993 |
| 6,945,961 | B2 | 9/2005 | Miller et al. | DE | 4419235 | 12/1995 |
| 7,008,399 | B2 | 3/2006 | Larsen et al. | DE | 19503230 | 8/1996 |
| 7,080,936 | B1 | 7/2006 | Simpson | DE | 29513214 | 2/1997 |
| 7,090,662 | B2 | 8/2006 | Wimpenny et al. | DE | 19723647 | 12/1998 |
| 7,094,221 | B2 | 8/2006 | Veasey et al. | DE | 19838760 | 4/2000 |
| 7,104,972 | B2 | 9/2006 | Moller et al. | DE | 29907880 | 9/2000 |
| 7,133,329 | B2 | 11/2006 | Skyggebjerg et al. | DE | 10103287 | 8/2001 |
| 7,175,055 | B2 | 2/2007 | Hansen et al. | DE | 10201875 | 5/2003 |
| 7,195,609 | B2 | 3/2007 | Huegli | DE | 10229122 | 2/2004 |
| 7,195,616 | B2 | 3/2007 | Diller et al. | DE | 20317377 | 4/2005 |
| 7,241,278 | B2 | 7/2007 | Moller | DE | 102004046003 | 3/2006 |
| 7,500,966 | B2 * | 3/2009 | Hommann ............... 604/211 | DK | 200100240 | 2/2001 |
| 7,678,084 | B2 | 3/2010 | Judson et al. | DK | 2005/00116 | 6/2005 |
| 7,704,238 | B2 | 4/2010 | Diller et al. | EP | 15617 | 9/1980 |
| 2001/0034506 A1 | | 10/2001 | Hirschman et al. | EP | 017318 | 10/1980 |
| 2001/0053893 A1 | | 12/2001 | Larsen | EP | 0064858 | 11/1982 |
| 2002/0002326 A1 | | 1/2002 | Causey, III et al. | EP | 327810 | 8/1989 |
| 2002/0007154 A1 | | 1/2002 | Hansen et al. | EP | 338806 | 10/1989 |
| 2002/0016571 A1 | | 2/2002 | Kirchhofer et al. | EP | 0362484 | 4/1990 |
| 2002/0020654 A1 | | 2/2002 | Eilersen | EP | 387854 | 9/1990 |
| 2002/0049415 A1 | | 4/2002 | Fukuda | EP | 422482 | 4/1991 |

| | | | | | |
|---|---|---|---|---|---|
| EP | 454331 | 10/1991 | RU | 2111019 | 5/1997 |
| EP | 327910 | 4/1992 | RU | 2091087 | 9/1997 |
| EP | 498737 | 8/1992 | RU | 2212254 | 9/2003 |
| EP | 879610 | 8/1992 | WO | WO8502256 | 5/1985 |
| EP | 0513128 | 11/1992 | WO | WO 87/02895 | 5/1987 |
| EP | 554996 | 8/1993 | WO | WO 89/07463 | 8/1989 |
| EP | 615762 | 3/1994 | WO | WO 90/09202 | 8/1990 |
| EP | 594349 | 4/1994 | WO | WO 91/10460 | 7/1991 |
| EP | 608343 | 9/1994 | WO | WO9110677 | 7/1991 |
| EP | 513128 | 7/1995 | WO | WO 9114467 | 10/1991 |
| EP | 0673482 | 9/1995 | WO | WO9301573 | 1/1993 |
| EP | 679440 | 11/1995 | WO | WO 9303780 | 3/1993 |
| EP | 702970 | 3/1996 | WO | WO 93/07922 | 4/1993 |
| EP | 1000631 | 10/1997 | WO | WO 9412228 | 6/1994 |
| EP | 0 608 343 B1 | 12/1997 | WO | WO9524233 | 9/1995 |
| EP | 554995 | 12/1997 | WO | WO 96/07443 | 3/1996 |
| EP | 295075 | 12/1998 | WO | WO 96/26754 | 9/1996 |
| EP | 897728 | 2/1999 | WO | WO 96/32973 | 10/1996 |
| EP | 0937471 | 8/1999 | WO | WO 96/38190 | 12/1996 |
| EP | 0937472 | 8/1999 | WO | WO 97/07841 | 3/1997 |
| EP | 0937476 | 8/1999 | WO | WO 9710865 | 3/1997 |
| EP | 1003581 | 8/1999 | WO | WO9730742 | 8/1997 |
| EP | 1351732 | 1/2001 | WO | WO9733638 | 9/1997 |
| EP | 1074273 | 2/2001 | WO | WO9734919 | 9/1997 |
| EP | 1095668 | 5/2001 | WO | WO 97/36695 | 10/1997 |
| EP | 0747391 | 3/2004 | WO | WO 98/10813 | 3/1998 |
| EP | 1462134 A1 | 9/2004 | WO | WO 98/56436 | 12/1998 |
| EP | 937476 | 1/2005 | WO | WO 9857688 | 12/1998 |
| EP | 1541185 | 6/2005 | WO | WO9907425 | 2/1999 |
| EP | 1557163 | 7/2005 | WO | WO 99/16487 | 4/1999 |
| EP | 1557189 | 7/2005 | WO | WO9915214 | 4/1999 |
| EP | 1 568 389 A1 | 8/2005 | WO | WO 9916487 | 4/1999 |
| EP | 1304129 | 11/2005 | WO | WO 9921598 | 5/1999 |
| EP | 1610848 | 1/2006 | WO | WO 9938554 | 8/1999 |
| EP | 1645301 | 4/2006 | WO | WO 9948546 | 9/1999 |
| EP | 1723977 | 11/2006 | WO | WO9965548 | 12/1999 |
| EP | 1728529 | 12/2006 | WO | WO0037129 | 6/2000 |
| EP | 1782853 | 5/2007 | WO | WO 00/51668 | 9/2000 |
| EP | 1819382 | 8/2007 | WO | WO 01/19434 | 3/2001 |
| EP | 2000161 | 12/2008 | WO | WO0126710 | 4/2001 |
| FR | 2583291 | 12/1986 | WO | WO 01/30425 | 5/2001 |
| FR | 2622457 | 5/1989 | WO | WO0172361 | 10/2001 |
| FR | 2697434 | 5/1994 | WO | WO 01/95959 | 12/2001 |
| FR | 2740345 | 4/1997 | WO | WO0205876 | 1/2002 |
| FR | 2 767 479 | 2/1999 | WO | WO0224257 | 3/2002 |
| FR | 2857654 | 1/2005 | WO | WO 02/053214 | 7/2002 |
| GB | 664044 A | 1/1952 | WO | WO02064196 | 8/2002 |
| GB | 2091107 | 7/1982 | WO | WO 02/076535 | 10/2002 |
| GB | 2153445 | 8/1985 | WO | WO 02/076536 | 10/2002 |
| GB | 2229497 | 9/1990 | WO | WO 02/092153 | 11/2002 |
| GB | 2309644 | 8/1997 | WO | WO03057283 | 7/2003 |
| GB | 0007071.4 | 3/2000 | WO | WO03063680 | 8/2003 |
| IN | 165367 | 3/1986 | WO | WO 03/080160 A1 | 10/2003 |
| JP | 56-163486 | 12/1981 | WO | WO03099357 | 12/2003 |
| JP | 57-000033 | 1/1982 | WO | WO 2004/002556 | 1/2004 |
| JP | 01-100495 | 4/1989 | WO | WO 2004/007002 A1 | 1/2004 |
| JP | 64-035671 | 6/1989 | WO | WO 2004004825 | 1/2004 |
| JP | 02071758 A | 3/1990 | WO | WO 2004/024218 | 3/2004 |
| JP | 02-126184 | 5/1990 | WO | WO 2004/028598 | 4/2004 |
| JP | 02-182267 | 7/1990 | WO | WO 2004/035113 A2 | 4/2004 |
| JP | 4-224764 | 8/1992 | WO | WO 2004/035113 A3 | 4/2004 |
| JP | 04256757 A | 9/1992 | WO | WO 2004/078239 | 9/2004 |
| JP | 4-507059 | 12/1992 | WO | WO 2004/078240 | 9/2004 |
| JP | 05-337179 | 12/1993 | WO | WO 2004/078241 | 9/2004 |
| JP | 06-055644 | 1/1994 | WO | WO 2004078242 | 9/2004 |
| JP | 06-034825 | 10/1994 | WO | WO2004080306 | 9/2004 |
| JP | 06-296691 | 10/1994 | WO | WO2004084795 | 10/2004 |
| JP | 7-500039 | 1/1995 | WO | WO2004095379 | 11/2004 |
| JP | 7-502678 | 3/1995 | WO | WO 2005018721 | 3/2005 |
| JP | 09166474 | 6/1997 | WO | WO 2005037352 | 4/2005 |
| JP | 11511364 | 10/1999 | WO | WO 2005/046770 | 5/2005 |
| JP | 3017167 | 11/1999 | WO | WO2005089835 | 9/2005 |
| JP | 2000237308 | 9/2000 | WO | WO2005097233 | 10/2005 |
| JP | 2003284777 | 10/2003 | WO | WO2005097240 | 10/2005 |
| JP | 2004-503303 | 2/2004 | WO | WO 2006039930 | 4/2006 |
| JP | 2004-516895 | 6/2004 | WO | WO 2006/045528 | 5/2006 |
| JP | 2005536300 A | 12/2005 | WO | WO 2006/045529 | 5/2006 |
| JP | 2006250582 | 9/2006 | WO | WO2006045425 | 5/2006 |
| JP | 2007-509662 | 4/2007 | WO | WO2006045525 | 5/2006 |

| WO | WO 2006/069454 | 7/2006 |
| WO | WO2006076921 | 7/2006 |
| WO | WO2006116997 | 11/2006 |
| WO | WO 2006/128794 | 12/2006 |
| WO | WO 2007/030957 | 3/2007 |
| WO | WO2007041843 | 4/2007 |
| WO | WO2007107558 | 9/2007 |
| WO | WO2007107561 | 9/2007 |
| WO | WO 2007/134954 | 11/2007 |
| WO | WO 2008/037801 | 4/2008 |
| WO | WO2008057223 | 5/2008 |

OTHER PUBLICATIONS

Answer in *Novo Nordisk A/S* v. *Sanofi-Aventis U.S. LLC* and Sanofi-Aventis downloaded from PACER on Feb. 29, 2008.
Complaint in *Novo Nordiks A/S* v. *Sanofi-Aventis U.S. LLC* and Sanofi-Aventis downloaded from PACER on Feb. 29, 2008.
Declaration of Benard Sams in *Novo Nordisk A/S* v. *Sanofi-Aventis U.S. LLC* and Sanofi-Aventis downloaded from PACER on Feb. 29, 2008.
International Search Report and Written Opinion issued in connection with counterpart PCT Application No. PCT/EP2006/061747 mailed Sep. 29, 2006.
International Search Report and Written Opinion issued in connection with counterpart PCT Application No. PCT/EP2006/061748 mailed Aug. 10, 2006.
May 17, 2002 Office Action in 09768760 and accompanying 892 and 1149 forms.
Opinion of US District Court for the District of NJ (Docket No. 3:07-cv-03206-MLC-JJH in *Novo Nordisk A/S* v. *Sanofi-Aventis U.S. LLC* and Sanofi-Aventis Denying motion of a preliminary injunction entered Feb. 20, 2008.
Print-out of file history of U.S. Appl. No. 10/610,926 which is owned by the same assignee as U.S. Appl. No. 11/765,789.
Search Report issued in connection with counterpart Danish Application No. PA 2005 00588 mailed Feb. 13, 2006.
Search Report issued in connection with counterpart Danish Application No. PA 2005 00589 mailed Feb. 16, 2006.
US Reissue U.S. Appl. No. 10/442,855.
US Reissue U.S. Appl. No. 10/960,900.
US Reissue U.S. Appl. No. 11/121,331.
US Reissue U.S. Appl. No. 11/640,610.
Written Opinion issued in connection with counterpart PCT Application No. PCT/EP2006/061747 mailed Nov. 8, 2006.
Written Opinion issued in connecton with counterpart PCT Application No. PCT/EP2006/061748 mailed Nov. 8, 2006.
Chia Kai Su et al, Process Biochemistry, 2006, vol. 41, Part 2, pp. 257-263.
Dennison, Clive et al, Protein Expression and Purification, 1997, vol. 11, Part 2, pp. 149-161.
English Abstract of DE3048135 Published Jul. 15, 1982.
English Translation for DE3609555.
English Abstract for DE4419235.
English Translation for EP679440 Published Nov. 2, 1995.
English Abstract for FR2583291.
English Abstract for FR2697434 Published May 6, 1994.
English Abstract for FR2767479.
English Abstract of JP06-034825 Published Oct. 2, 1994.
English Abstract of JP06-055644 Published Jan. 3, 1994.
English Abstract of JP57-000033 Published Jan. 5, 1982.
English Abstract of JP64-035671 Published Jun. 2, 1989.
English Abstract for JP 2000237308 Published Sep. 5, 2000.
English Abstract for JP 2003284777 Published Oct. 7, 2003.
English Abstract for JP2005337179.
English Abstract for JP2006296691.
Fransson et al, Pharmaceutical Research, 1997, vol. 14, Part 5, pp. 606-612.
Leonil et al, Enzyme and Microbiol Technology, 1994, vol. 16, Part 7, pp. 591-595.
Paule, B.J.A. et al, Protein Expression and Purification, 2004, vol. 34, Part 2, pp. 311-316.
Office Action Mailed Mar. 17, 1999 in U.S. Appl. No. 08/973,109, filed June 3, 1996 by Klitmose.
Notice of Allowance Mailed Oct. 25, 1999 in U.S. Appl. No. 08/973,109, filed Jun. 3, 1996 by Klitmose.
Office Action Mailed Apr. 26, 1999 in U.S. Appl. No. 09/090,144, filed Jun. 4, 1998 by Klitmose.
Final Action Mailed Dec. 20, 1999 in U.S. Appl. No. 09/090,114, filed Jun. 4, 1998 by Klitmose.
Notice of Allowance Mailed Apr. 6, 2004 in U.S. Appl. No. 09/090,144, filed Jun. 4, 1998 by Klitmose.
Non-Final Office Action Mailed Aug. 27, 2002 in U.S. Appl. No. 09/882,536, filed Jun. 14, 2001 by Moller et al.
Notice of Allowance Mailed Jun. 17, 2003 in U.S. Appl. No. 09/882,536, filed Jun. 4, 2001 by Moller et al.
Notice of Allowance Mailed on Apr. 23, 2007 in U.S. Appl. No. 10/667,040, filed Sep. 22, 2003 by Moller et al.
Office Action Mailed Mar. 17, 2008 in U.S. Appl. No. 11/122,289, filed May 4, 2005 by Moller et al.
Non-Final Rejection Mailed on Dec. 15, 2008 in U.S. Appl. No. 11/122,289, filed May 4, 2005 by Moller et al.
Final Action Mailed Nov. 5, 2009. In U.S. Appl. No. 11/122,289, filed May 4, 2005 by Moller et al.
Advisory Action Mailed on Mar. 23, 2010 in U.S. Appl. No. 11/122,289, filed May 4, 2005 by Moller et al.
Office Action Mailed on Mar. 14, 2008 in U.S. Appl. No. 11/765,789, filed Jun. 20, 2007 by Moller et al.
Office Action Mailed on Dec. 17, 2008 in U.S. Appl. No. 11/765,789, filed Jun. 20, 2007 by Moller et al.
Final Action Mailed on Nov. 5, 2009 in U.S. Appl. No. 11/765,789, filed Jun. 20, 2007 by Moller et al.
Office Action Mailed on Jan. 15, 2010 in U.S. Appl. No. 11/930,926, filed Oct. 31, 2007 by Moller et al.
Office Action Mailed From the USPTO on Apr. 2, 2009 in U.S. App. No. 11/930,926, filed Oct. 31, 2007 by Moller et al.
Office Action Mailed on Apr. 2, 2009 in U.S. Appl. No. 11/931,010, filed Oct. 31, 2007 by Moller et al.
Final Office Action Mailed on Jan. 15, 2010 in U.S. Appl. No. 11/931,010, filed Oct. 31, 2007 by Moller et al.
Office Action Mailed on Sep. 15, 2004 in U.S. Appl. No. 10/646,295, filed Aug. 22, 2003 by Hansen et al.
Final Action Mailed on Feb. 8, 2005 in U.S. Appl. No. 10/646,295, filed Aug. 22, 2003 by Hansen et al.
Advisory Action Mailed Jul. 1, 2005 in U.S. Appl. No. 10/646,295, filed Aug. 22, 2003 by Hansen et al.
Office Action Mailed on Aug. 29, 2005 in U.S. Appl. No. 10/646,295, filed Aug. 22, 2003 by Hansen et al.
Final Office Action Mailed on Apr. 14, 2006 in U.S. Appl. No. 10/646,295, filed Aug. 22, 2003 by Hansen et al.
Notice of Allowance Mailed on Sep. 29, 2006 in U.S. Appl. No. 10/646,295, filed Aug. 22, 2003 by Hansen et al.
Office Action Mailed on Jan. 8, 2009 in U.S. Appl. No. 11/911,869, filed Oct. 18, 2007 by Glejbol et al.
Final Office Action Mailed on Sep. 29, 2009 in U.S. Appl. No. 11/911,869, filed October 18, 2007 by Glejbol et al.
Abandonment Mailed on Oct. 8, 2009 in U.S. Appl. No. 11/911,869, filed Oct. 18, 2007 by Glejbol et al.
Office Action Mailed on Apr. 1, 2009 in U.S. Appl. No. 11/911,871, filed Oct. 18, 2007 by Glejbol et al.
Abandonment Mailed on Nov. 6, 2009 in U.S. Appl. No. 11/911,871, filed Oct. 18, 2007 by Glejbol et al.
Non-Final Rejection Mailed on Jun. 8, 2010 in U.S. Appl. No. 12/571,721, filed Oct. 1, 2009 by Glejbol et al.
Office Action Mailed Jul. 20, 2010 in U.S. Appl. No. 12/300,675, filed May 3, 2007 by Moller et al.
Non-Final Rejection of Oct. 7, 2008 in U.S. Appl. No. 10/508,104 (US Patent No. 7,678,084; Issue Date Mar. 16, 2010), filed Sep. 15, 2004; First Named Inventor: Jared Alden Judson.
Non-Final Rejection of Mar. 19, 2009 in U.S. Appl. No. 10/508,104 (US Patent No. 7,678,084; Issue Date March 16, 2010), filed Sep. 15, 2004; First Named Inventor: Jared Alden Judson.
Abstract of AU2003232576.
English Abstract of DE10201875 Published May 22, 2003.
English Abstract of DE102004046003 Published Mar. 30, 2006.
English Abstract of DE19503230 Published Aug. 8, 1996.
English Abstract of DE3236374 Published Apr. 5, 1984.

English Abstract of DE3923079 Published Jan. 24, 1991.
English Abstract of EP387854 Published Sep. 19, 1990.
English Abstract of EP422482 Published Apr. 17, 1991.
English Abstract of FR2622457 Published May 5, 1989.
English Abstract of FR2740345 Published Apr. 30, 1997.
English Abstract of IN165367 Published Mar. 20, 1986.
English Abstract of JP01-100495 Published Apr. 18, 1989.
Machine Translation of JP09166474 Published Jun. 24, 1997.
English Abstract of JP02-126184 Published May 15, 1990.
English Abstract of JP02-182267 Published Jul. 16, 1990.
English Abstract of JP2006250582 Published Sep. 21, 2006.
English Abstract of JP3017167 Published Nov. 30, 1999.
English Abstract of JP4-224764 Published Aug. 14, 1992.
English Abtsract of JP4-507059 Published Dec. 10, 1992.
English Abstract of JP56-163486 Published Dec. 16, 1981.
English Abstract of JP 7-500039 Published Mar. 14, 1994.
English Abstract of RU2091087.
English Abstract of RU2212254.
Annersten, M. et al., Insulin Pens Dribble From the Tip of the Needle After Injection, Practical Diabetes Int., vol. 17(4), pp. 109-111 (2000).
Beckmann, Sensors, Memory, Circuits, Polyapply Newsletter, vol. 1(3), (2006).
Common Insulin Injection Challenges: http://www.bd.com/us/diabetes/page.ASPX?CAT=7001&ID=7265.
Gnanalingham, M.G. et al., Accuracy and Reproducibility of Low Dose Insulin Administration Using Pen-Injectors and Syringes, Downloaded From adc.bmj.com on Jan. 9, 2008.
Owen Mumford Product Range.
Search Report Issued in Connection With PCT Appln. No. PCT/EP2007/052630, Mailed Nov. 12, 2007.
Search Report Issued in Connection With European Application No. 06005599.3, Mailed Oct. 4, 2006.
Search Report Issued in Connection With PCT Application No. PCT/EP2007/052633, Mailed Feb. 20, 2008.
Search Report Issued in Connection With European Appln No. 06005602.5, Mailed Oct. 16, 2006.
Trankler, Hans-Rolf, R. Oldenbourg, Verlag, Munchen, Wien.
Notice of Opposition by Owen Mumford (UK).
Notice of Opposition by Genentech (USA).
Notice of Opposition by Techpharma (CH) Including English Translation.
Opposition in Related European Patent Application EP 02711784.5 of Sep. 19, 2008.
Validity Opinion by the UK PTO.

* cited by examiner

INJECTION DEVICE AND A METHOD OF CHANGING A CARTRIDGE IN THE DEVICE

CROSS-REFERENCE TO RELATED APPLICATIONS

This application is a 35 U.S.C. §371 national stage application of International Patent Application PCT/EP2007/051757 (published as WO 2007/104636), filed Feb. 23, 2007, which claimed priority of European Patent Application 06004933.5, filed Mar. 10, 2006; this application further claims priority under 35 U.S.C. §119 of U.S. Provisional Application 60/784,779, filed Mar. 22, 2006.

FIELD OF THE INVENTION

The present invention relates to an injection device in which it is possible to exchange an empty cartridge with a new cartridge containing a liquid drug to be injected into a person. Such an injection device is also known as a refillable injection device. More particularly, the present invention relates to an injection device with a dose setting mechanism comprising a dose rod. The injection device of the present invention is particularly suitable for repetitive self-injection, e.g. of insulin or growth hormone. The injection device may preferably be in the form of a so-called injection pen. The present invention further relates to a method of changing a cartridge in such an injection device.

BACKGROUND OF THE INVENTION

When changing the cartridge of a refillable injection device it is desirable to let the piston of the new cartridge push the piston rod of the injection device back into the injection device. Thereby it is ensured that the piston rod contacts the piston when the cartridge is positioned correctly, and the injection device is therefore ready for use. Thereby the need for very large air shots before taking the injection device into use is avoided.

However, in prior art refillable injection devices having a dose rod, the piston rod is pushed, pulled or rotated back manually, thereby introducing the problem that it can not be ensured that the piston rod contacts the piston, and very large air shots are therefore necessary in order to ensure correct use of the injection device.

In order to ensure proper operation of the injection device during setting of a desired dose, the dose rod and a dose setting member must be rotationally locked when the cartridge is positioned correctly. This is usually obtained by letting the dose rod and the dose setting member engage, e.g. by means of mating sets of teeth positioned on the dose rod and the dose setting member, respectively. This may cause stress to be introduced in the piston rod, and this tension may have the consequence that liquid drug will be expelled from the injection device when a needle is subsequently attached to the new cartridge.

In WO 02/092153 an attempt to solve the above mentioned problem is disclosed. Thus, WO 02/092153 discloses a medication injector apparatus, such as an injection pen. The injection pen includes a resettable cartridge plunger drive assembly including an axially floating nut, a cartridge plunger engaging screw, and a drive clutch movable with the nut and which when rotated causes the screw to screw through the nut. When a cartridge assembly is mounted to the pen base, the floating nut and drive clutch are shifted proximally such that the drive clutch is in torque transmitting engagement with a rotatable drive member of the pen, such that rotation of that drive member results in drive screw advancement through the nut in the distal direction. When the cartridge assembly is not mounted to the pen base, the floating nut and drive clutch are biased distally to disengage the drive clutch from torque transmitting engagement with the rotatable drive member and to thereby allow the drive screw to be reset proximally through the nut to a position more retracted within the pen base. Thereby drooling of the pen is limited.

The injection device of WO 02/092153 is not of the kind having a dose setting mechanism comprising a dose rod, and the mechanism disclosed therein is not suitable for use in such an injection device.

SUMMARY OF THE INVENTION

It is, thus, an object of the invention to provide an injection device of the kind having a dose setting mechanism comprising a dose rod, and in which the above mentioned problems of introducing stress in the piston rod are avoided, or at least minimised.

According to a first aspect of the invention, the above and other objects are fulfilled by providing an injection device comprising:

a dose setting mechanism operable to set a desired dose, the dose setting mechanism comprising a dose setting member and a dose rod, the dose setting mechanism being adapted to be in a first position in which the dose setting member and the dose rod engage, and a second position in which the dose setting member and the dose rod do not engage, the dose setting mechanism being in the first position during normal operation of the injection device, and in the second position during cartridge change,
 a piston rod adapted to cooperate with a piston in a cartridge in order to expel a dose of liquid from the cartridge,
 an injection mechanism operable to cause the piston rod and the piston to expel a previously set dose of liquid from the cartridge, and
 a cartridge holder for releasably holding a cartridge,
wherein the cartridge holder is operatively connected to the dose rod in such a manner that when a cartridge is being inserted in the cartridge holder, the dose rod is caused to move along with the piston rod in an at least substantially axial direction, at least while the dose setting mechanism is moved from the second position to the first position.

The injection device is preferably of the kind having an elongated shape, i.e. a so-called injection pen.

The dose setting mechanism comprises a dose setting member and a dose rod. The dose setting member is a part of the dose setting mechanism which is actually operated by the user during setting of a desired dose, e.g. by dialling the dose setting member or pulling it in a direction away from a housing enclosing the injection device. The dose setting member may, thus, be or comprise a dose knob, such as a rotatable dose knob. The dose setting member is preferably positioned at or near a proximal end of the injection device, i.e. opposite the end where an injection needle would normally be positioned.

The dose rod is an elongated part extending along a longitudinal direction of the injection device. When the dose setting member is operated to set a desired dose, the dose rod is caused to move along with the dose setting member, preferably in a rotational movement. The dose rod thereby causes the injection mechanism to be moved to a position where it is ready for causing injection of the set dose. This may, e.g., be done by moving an injection button in a proximal direction, as will be further explained below. The dose rod preferably extends from the dose setting member to a position at or near a proximal end of the cartridge holder.

During normal operation of the injection device, the dose setting mechanism is adapted to be in a first position in which the dose setting member and the dose rod engage. Thereby it is ensured that when a user operates the dose setting member, the desired dose is actually set. When the cartridge is being changed, on the other hand, the dose setting mechanism is in a second position in which the dose setting member and the dose rod do not engage. Thus, during cartridge change the dose setting member and the dose rod are allowed to move independently, preferably in a rotational manner. Accordingly, when a new cartridge is being inserted, the dose setting mechanism will need to be moved from the second position to the first position during this operation, i.e. the dose setting member and the dose rod need to be moved into engagement. As mentioned above, the dose rod will be prevented from performing a rotational movement relatively to the dose setting member during this operation. This will be described further below.

The injection mechanism preferably comprises an injection button which is moved in a proximal direction during setting of a desired dose. When the set dose is subsequently injected, the user pushes the injection button in a distal direction, i.e. in a direction opposite the direction in which it was moved during setting of the dose. The injection button is, in this case, connected to the piston in such a manner that moving the injection button in the distal direction causes the piston rod to also be moved in the distal direction, possibly with a suitable gearing. Since the piston rod cooperates with the piston of the cartridge, preferably by abutting the piston, the piston is moved a corresponding distance, and the set dose is thereby expelled from the cartridge.

The cartridge holder is releasably holding a cartridge. This should be interpreted to mean that it is possible to remove the cartridge from the cartridge holder, e.g. when the cartridge is empty, and replace it by another cartridge. Thus, the injection device is of the refillable kind. However, during normal operation of the injection device, the cartridge holder should be positioned in such a manner that it is not possible to remove the cartridge. Furthermore, the cartridge holder is preferably movable relatively to the remaining parts of the injection device during change of cartridge. In this embodiment the cartridge holder, holding the cartridge, is at least partly removed from the injection device, the cartridge is replaced by a new cartridge, and the cartridge holder, holding the new cartridge, is inserted into the injection device.

The cartridge holder is operatively connected to the dose rod. This has the consequence that when a new cartridge is being inserted in the injection device by means of the cartridge holder, the dose rod is caused to move along with the piston rod in an at least substantially axial direction while the dose rod and the dose setting member are moved into engagement. As mentioned above, the piston rod is pushed in a proximal direction by the piston of the new cartridge during insertion of the cartridge. By causing the dose rod to move along with the piston rod while the dose rod and the dose setting member are moved into engagement, and the dose rod is therefore prevented from rotating relatively to the dose setting member, the piston rod is allowed to continue its axial movement. Thereby a build-up of stress in the piston rod is prevented, and when an injection needle is subsequently inserted in the cartridge, no drug will be expelled due to such a stress. This is very advantageous.

This may advantageously be obtained in the following manner. When the new cartridge is being inserted in the injection device, the piston of the cartridge pushes the piston rod back. During this movement a nut will cause the dose rod to perform a rotational movement. When the cartridge is almost in position, the cartridge holder pushes a carrier which is also connected to the nut. Thereby the nut is also pushed back. Accordingly, the dose rod and the nut will be moved back in an axial direction with the same velocity, and the nut will therefore no longer cause a rotational movement of the dose rod. Thereby the dose rod and the dose setting member may be moved into engagement without the risk of introducing stress in the piston rod.

The first position of the dose setting mechanism may be defined by engagement of a set of teeth positioned on the dose setting member and a mating set of teeth positioned on the dose rod. In this case the dose rod will be prevented from rotating relatively to the dose setting member as soon as the mating teeth start to move into engagement. From this point until the teeth have been moved fully into engagement, the dose rod is moved along with the piston rod as described above.

The cartridge holder may comprise a cartridge holding member comprising a set of jaws adapted to clamp a distal end of a cartridge. In this embodiment the cartridge is held by the cartridge holder by means of the set of jaws. The set of jaws is preferably movable in such a manner, that during normal operation of the injection device they firmly clamp the cartridge, thereby securing it with respect to the remaining parts of the injection device. During cartridge change, on the other hand, the jaws may be moved to a position in which they release the grip on the cartridge, thereby allowing one cartridge to be removed from and another to be positioned in the cartridge holder. The injection device in this case preferably comprises a releasable locking mechanism which locks the jaws in the clamping position during normal operation of the injection device, and which may be operated to release the grip when it is desired to replace the cartridge.

Alternatively, the cartridge holder may comprise a frame member adapted to carry the cartridge, and the cartridge may be moved along with and by means of the frame member during cartridge change. According to this embodiment the cartridge holder is preferably in the form of a 'drawer' in which the cartridge may be positioned. When a cartridge is removed from the injection device the complete frame member is pulled at least partly out of the injection device. The cartridge is removed, a new cartridge is positioned in the frame member, and the complete frame member, holding the new cartridge, is repositioned in the injection device.

The injection device may further comprise a biasing mechanism causing the dose setting mechanism to be in the second position when no cartridge is positioned in the cartridge holder, and when the cartridge holder is open. Thereby the dose setting member and the dose rod will automatically be moved out of engagement when the cartridge is being replaced. The biasing mechanism may advantageously comprise a spring member.

According to a second aspect of the invention, the above and other objects are fulfilled by providing a method of changing a cartridge in an injection device, the injection device comprising a dose setting mechanism operable to set a desired dose, the dose setting mechanism comprising a dose setting member and a dose rod, the dose setting member being adapted to be in a first position in which the dose setting member and the dose rod engage, and a second position in which the dose setting member and the dose rod do not engage, the injection device further comprising a cartridge holder being operatively connected to the dose rod, the method comprising the steps of:

moving the cartridge holder holding an empty cartridge in such a manner that the empty cartridge is accessible, and in such a manner that the dose setting mechanism is caused to move from the first position to the second position, removing the empty cartridge from the cartridge holder, inserting a new cartridge into the cartridge holder, moving the cartridge holder holding the new cartridge in such a manner that a piston rod of the injecting device is moved along with a piston of the new cartridge, and moving the dose setting mechanism from the second position to the first position while causing the dose rod to move along with the piston rod in an at least substantially axial direction.

It should be noted that a person skilled in the art would readily recognise that any feature which has been described in combination with the first aspect could also be combined with the second aspect, and vice versa.

The method according to the second aspect of the invention is, thus, performed using an injection device according to the first aspect of the invention.

BRIEF DESCRIPTION OF THE DRAWINGS

The invention will now be described in further details with reference to the accompanying drawings in which.

DETAILED DESCRIPTION OF THE DRAWINGS

Figure 1:
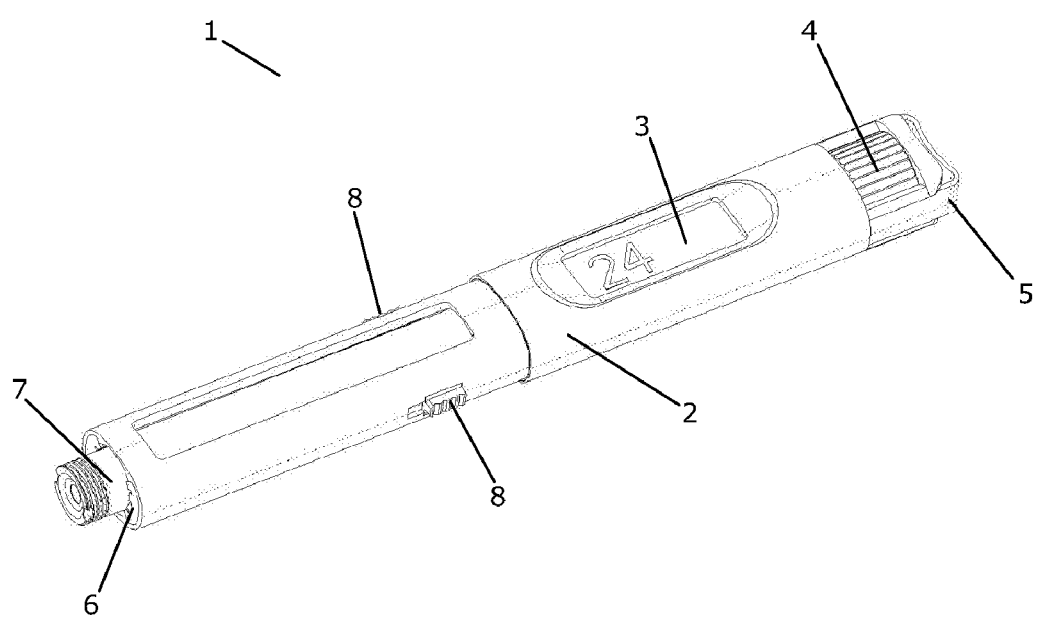
FIG. 1 is a perspective view of an injection device according to an embodiment of the invention, the injection device being in a position in which it is ready for operation.

FIG. 1 is a perspective view of an injection device 1 according to an embodiment of the invention. The injection device 1 comprises a housing 2 with a display 3 mounted thereon. The display 3 may show the amount of drug left in a cartridge, a set dose, etc. The injection device 1 further comprises a dose setting member 4 being rotationally operable to set a desired dose, and an injection button 5 being operable to cause a set dose to be expelled from the injection device 1. Furthermore, the injection device 1 comprises a cartridge holder 6 for releasably holding a cartridge 7. The cartridge holder 6 may be released by means of release buttons 8. In FIG. 1 the injection device 1 is in a position in which it is ready for setting a dose, i.e. a cartridge 7 is positioned in the cartridge holder 6, and the cartridge holder 6 has not been released.

Figure 2:
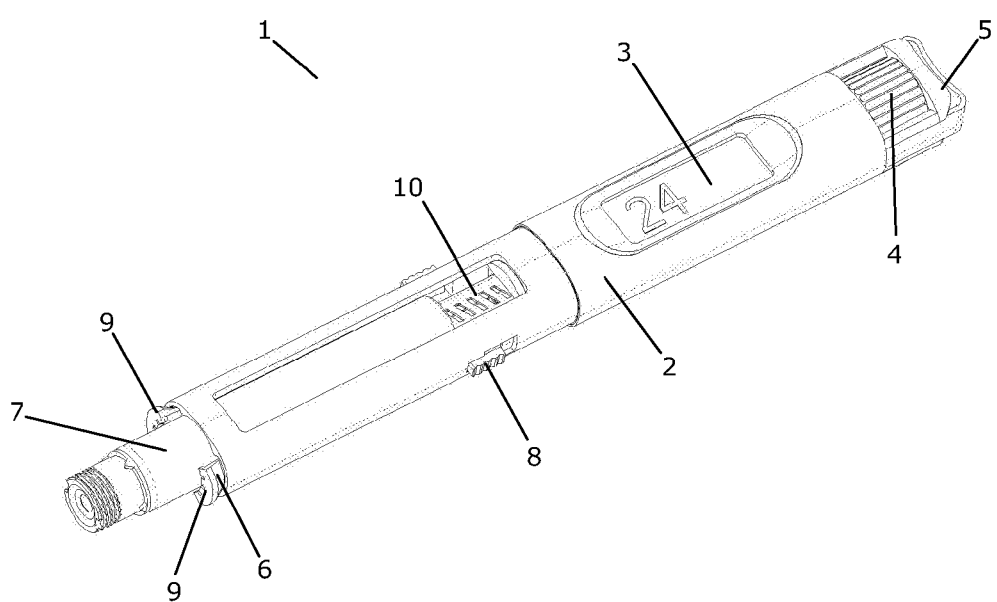
FIG. 2 is a perspective view of the injection device of FIG. 1, in which an old cartridge is about to be removed.

FIG. 2 is a perspective view of the injection device 1 of FIG. 1. In FIG. 2 the cartridge 7 is being exchanged. Thus, the release buttons 8 have been pushed in order to release the cartridge holder 6. Thereby a set of jaws 9 of the cartridge holder 6 has been moved out of the housing 2, and the jaws 9 are no longer gripping the cartridge 7 firmly. Accordingly, the cartridge 7 can be removed from the injection device 1. In FIG. 2 the cartridge 7 has been pulled partly out. A piston rod 10 is visible.

Figure 3:
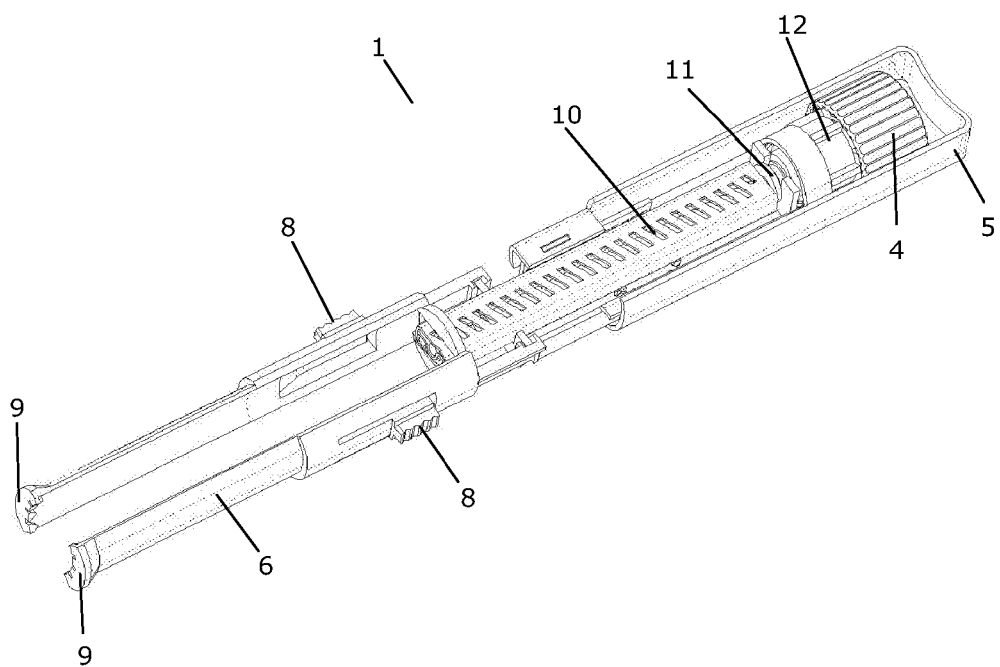
FIG. 3 shows selected parts of the injection device of FIGS. 1 and 2 in a position where it is ready for normal operation.

FIG. 3 shows selected parts of the injection device 1 of FIGS. 1 and 2. For clarity only the parts which are essential for explaining the change of cartridge are shown, the remaining parts being omitted. FIG. 3 corresponds to FIG. 1 in that it shows the injection device 1 in a position where it is ready for use. The jaws 9 of the cartridge holder 6 are in a position where they are adapted to clamp a cartridge firmly. The piston rod 10 is positioned as close to the dose setting member 4 as possible, indicating that the cartridge (not shown) is full, i.e. it has just been inserted in the injection device 1. In FIG. 3 a dose rod 11 is further visible. The dose rod 11 and the dose setting member 4 engage at a position which is hidden by member 12. This will be explained below with reference to FIG. 5.

Figure 4:
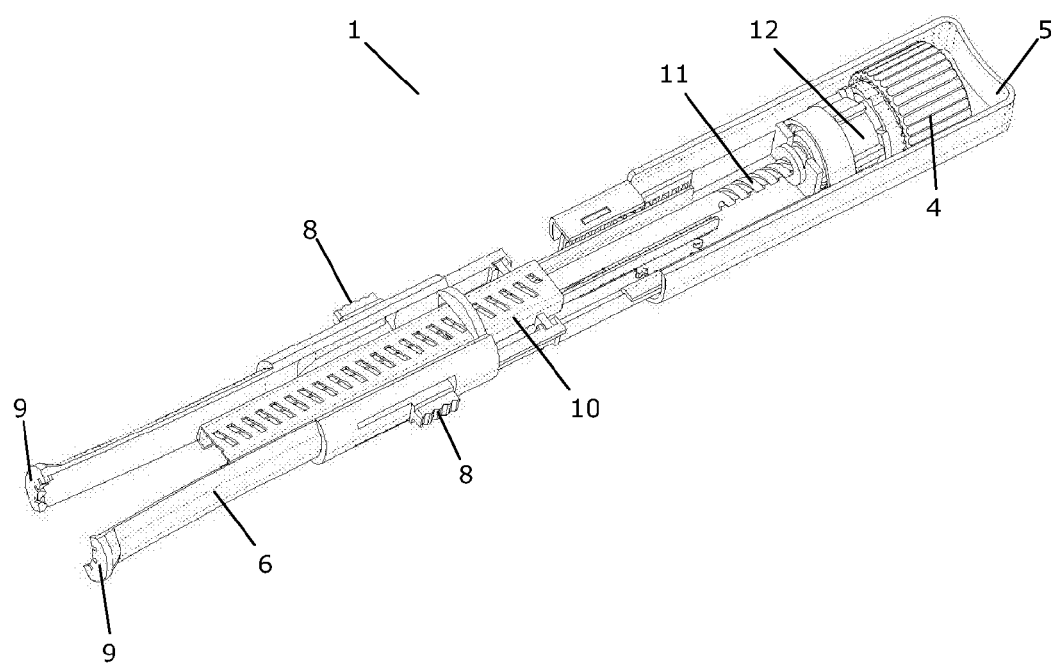
FIG. 4 shows selected parts of the injection device of FIGS. 1-3 during insertion of a new cartridge.

FIG. 4 shows selected parts of the injection device 1 of FIGS. 1-3. FIG. 4 corresponds to FIG. 2 in that it shows the injection device 1 during a cartridge change. The jaws 9 of the cartridge holder 6 are positioned further apart than is the case in FIG. 3, thereby indicating that they have been released by means of the release buttons 8, and that they are therefore no longer firmly gripping a cartridge. The piston rod 10 is shown in a position which is relatively far from the dose setting member 4, thereby indicating that a cartridge has been emptied. In FIG. 4 the dose rod 11 is more clearly visible than in FIG. 3.

Figure 5:
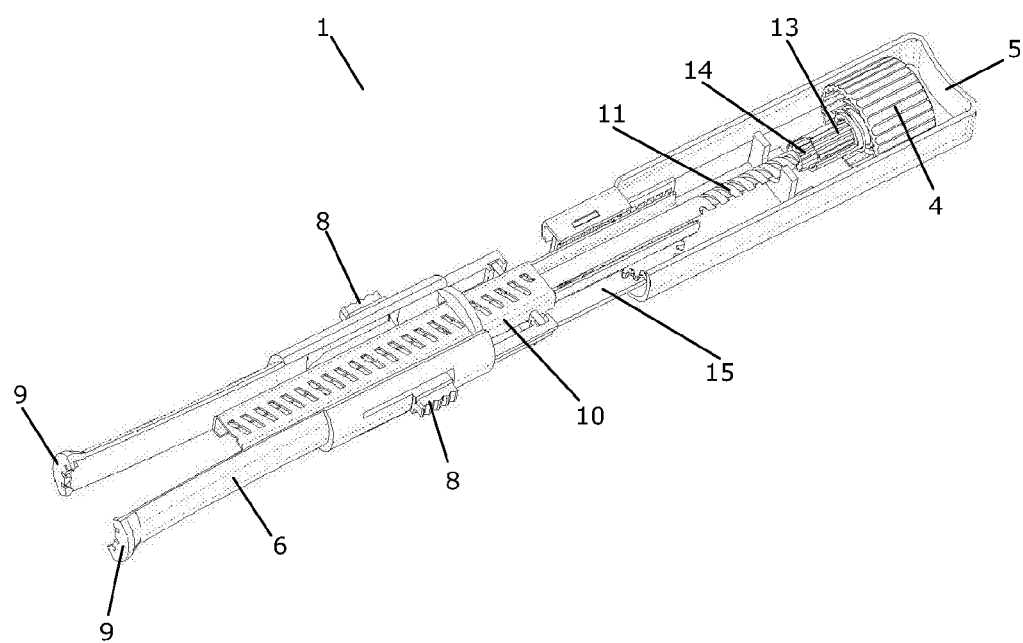
FIG. 5 shows the injection device of FIG. 4 with an additional part removed.

FIG. 5 shows the injection device 1 of FIG. 4 with the only exception that member 12 has been removed. Thereby it is possible to see that the dose setting member 4 is provided with a first set of teeth 13, and the dose rod 11 is provided with a second set of teeth 14. The second set of teeth 14 is adapted to slide into the first set of teeth 13, thereby causing the dose setting member 4 and the dose rod 11 to engage. As soon as the teeth 13, 14 start to engage, the dose rod 11 can no longer rotate relatively to dose setting member 4.

When a new cartridge is being inserted into the injection device 1, it is positioned between the jaws 9 and moved into the injection device 1. During this movement the piston of the cartridge will push the piston rod 10 backwards from the position shown in FIG. 5, and the dose rod 11 will rotate. When the cartridge is almost in position, it will press against the cartridge holder 6 which is thereby moved into the injection device 1. The cartridge holder 6 thereby presses against a carrier 15 which, via a nut (16, not shown in FIG. 5), prevents further rotation of the dose rod 11. The teeth 13, 14 are then moved into engagement by means of an axial movement of the dose rod 11. Thereby it is ensured that no stress is build-up in the piston rod 10.

Figure 6:
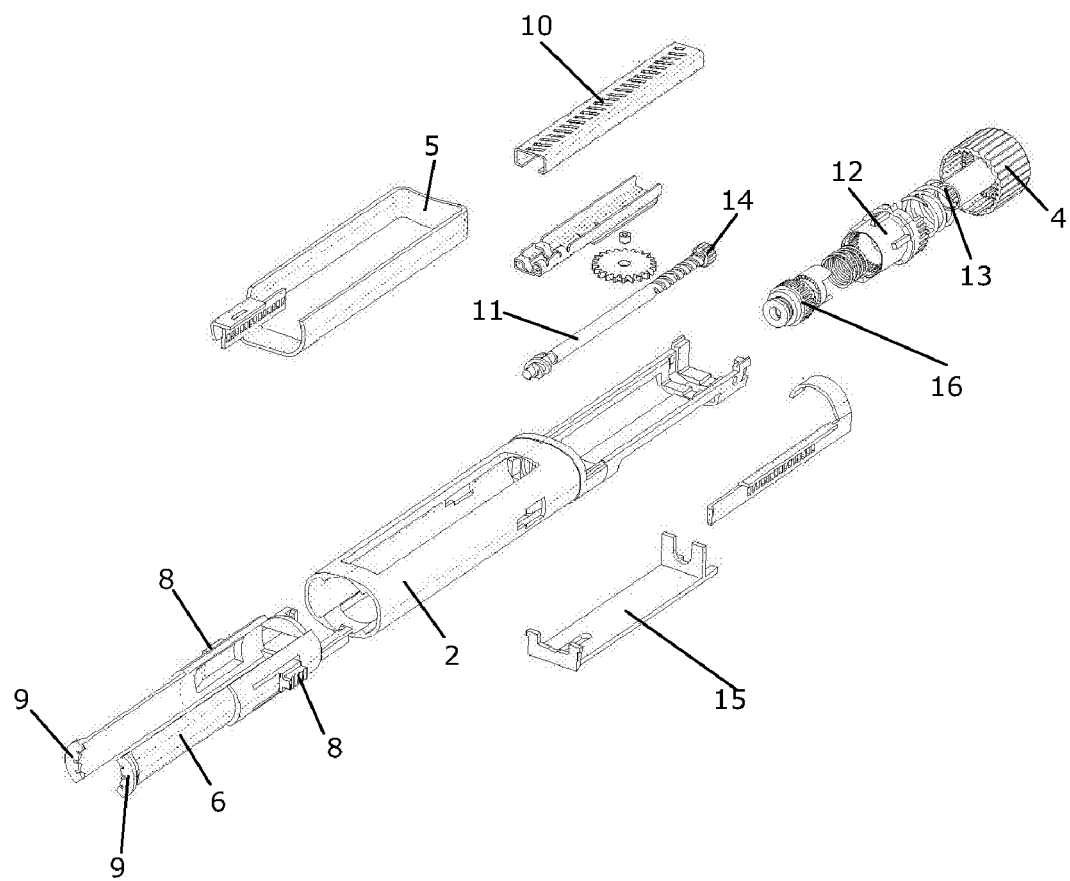
FIG. 6 is an exploded view of selected parts of the injection device of FIGS. 1-5.

FIG. 6 is an exploded view of selected parts of the injection device 1 of FIGS. 1-5.

The invention claimed is:

1. An injection device comprising:
 a dose setting mechanism operable to set a desired dose, the dose setting mechanism comprising a dose setting member and a dose rod, the dose setting mechanism being adapted to be in:
  a first position during normal operation of the injection device in which the dose setting member and the dose rod engage so that the dose rod moves along with the dose setting member, and
  a second position during cartridge change in which the dose setting member and the dose rod do not engage thereby allowing the dose setting member and the dose rod to move independently,
 a piston rod cooperating with the dose rod and adapted to cooperate with a piston in a cartridge in order to expel a dose of liquid from the cartridge,
 an injection mechanism operable to cause the piston rod and the piston to expel a previously set dose of liquid from the cartridge, and
 a cartridge holder for releasably holding a cartridge,
 wherein the cartridge holder is operatively connected to the dose rod in such a manner that when a cartridge is being inserted in the cartridge holder, the dose rod is caused to move along with the piston rod in an at least substantially axial direction, at least while the dose setting mechanism is moved from the second position to the first position.

2. An injection device according to claim 1, wherein the first position of the dose setting mechanism is defined by teeth positioned on the dose setting member being engaged to teeth positioned on the dose rod.

3. An injection device according to claim 2, wherein the cartridge holder comprises a cartridge holding member comprising a set of jaws adapted to clamp a distal end of a cartridge.

4. An injection device according to claim 2, wherein the cartridge holder comprises a frame member adapted to carry the cartridge, wherein the cartridge is moved along with and by means of the frame member during cartridge change.

5. An injection device according to claim 2, further comprising a biasing mechanism causing the dose setting mechanism to be in the second position when no cartridge is positioned in the cartridge holder.

6. An injection device according to claim 1, wherein the cartridge holder comprises a cartridge holding member comprising a set of jaws adapted to clamp a distal end of a cartridge.

7. An injection device according to claim 6, further comprising a biasing mechanism causing the dose setting mechanism to be in the second position when no cartridge is positioned in the cartridge holder.

8. An injection device according to claim 1, wherein the cartridge holder comprises a frame member adapted to carry the cartridge, wherein the cartridge is moved along with and by means of the frame member during cartridge change.

9. An injection device according to claim 8, further comprising a biasing mechanism causing the dose setting mechanism to be in the second position when no cartridge is positioned in the cartridge holder.

10. An injection device according to claim 1, further comprising a biasing mechanism causing the dose setting mechanism to be in the second position when no cartridge is positioned in the cartridge holder.

11. An injection device according to claim 1, wherein during independent movement between the dose rod and the dose setting mechanism, at least one of the dose rod and the dose setting mechanism moves rotationally.

12. A method of changing a cartridge in an injection device, the injection device comprising a dose setting mechanism operable to set a desired dose, the dose setting mechanism comprising a dose setting member and a dose rod, the dose setting mechanism being adapted to be in:
 a first position during normal operation in which the dose setting member and the dose rod engage so that the dose rod moves along with the dose setting member, and
 a second position during cartridge change in which the dose setting member and the dose rod do not engage thereby allowing the dose setting member and the dose rod to move independently,
the injection device further comprising a piston rod cooperating with the dose rod and comprising a cartridge holder being connected to the dose rod, the method comprising:
moving the cartridge holder holding a cartridge desired to be replaced in such a manner that the cartridge is accessible, and in such a manner that the dose setting mechanism is caused to move from the first position to the second position,
removing the cartridge from the cartridge holder,
inserting a new cartridge into the cartridge holder,
moving the cartridge holder holding the new cartridge in such a manner that a piston rod of the injection device is moved along with a piston of the new cartridge, and
moving, by the cartridge holder, the dose rod and the piston rod, the dose setting mechanism from the second position to the first position while causing the dose rod to move along with the piston rod in an at least substantially axial direction.

13. The method of claim 12, wherein during independent movement between the dose rod and the dose setting mechanism, at least one of the dose rod and the dose setting mechanism moves rotationally.

* * * * *

UNITED STATES PATENT AND TRADEMARK OFFICE
CERTIFICATE OF CORRECTION

| | | |
|---|---|---|
| PATENT NO. | : 8,298,194 B2 | Page 1 of 1 |
| APPLICATION NO. | : 12/282442 | |
| DATED | : October 30, 2012 | |
| INVENTOR(S) | : Moeller et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 711 days.

Signed and Sealed this
Twenty-sixth Day of August, 2014

Michelle K. Lee
*Deputy Director of the United States Patent and Trademark Office*